United States Patent [19]

Suzuki et al.

[11] Patent Number: 4,773,395
[45] Date of Patent: Sep. 27, 1988

[54] ENDOSCOPE

[75] Inventors: Akira Suzuki; Hiroaki Kubokawa; Nobuyuki Matsuura; Koji Kambara; Shigeru Nakajima; Hisao Yabe; Tatsuya Yamaguchi, all of Tokyo, Japan

[73] Assignee: Olympus Optical Co., Ltd., Tokyo, Japan

[21] Appl. No.: 48,895

[22] Filed: May 12, 1987

[51] Int. Cl.⁴ ............................................. A61B 1/00
[52] U.S. Cl. ........................................ 128/4; 138/120
[58] Field of Search .................... 128/3, 4, 5, 6, 7; 138/120

[56] References Cited

U.S. PATENT DOCUMENTS

| 3,557,780 | 1/1971 | Sato | 128/4 |
| 4,108,211 | 8/1978 | Tanaka | 128/4 X |
| 4,351,323 | 9/1982 | Ouchi et al. | 128/4 |

FOREIGN PATENT DOCUMENTS 60-32903  6/1985  Japan .

Primary Examiner—William H. Grieb
Attorney, Agent, or Firm—Ladas & Parry

[57] ABSTRACT

An endoscope according to the present invention comprises an observation optical system and an insertion section which includes a bending tube. A plurality of segments, which are rockably connected to one another, are arranged in the bending tube, and wire guides are fixed to the inner peripheral surface of each segment. One end of each of bending-control wires is fixed to the segment at the distal end portion of the bending tube. The other end of each wire extends to the proximal end portion of the insertion section, through the wire guides of the other segments. In this arrangement, the bending tube is bent by pulling the other ends of the bending-control wires. The endoscope further includes bending means arranged in the bending tube and adapted to bend, when the bending-control wire is pulled, the bending tube for moving the observation optical system such that the center of the system moves from the center of the insertion section to the periphery thereof. Thus, even though the bending tube is bent sharply, the position of a flexible tube of the insertion section, which may possibly obstruct the field of view, can be shifted to the right or left from the center of the field, thereby keeping the view field entire.

5 Claims, 5 Drawing Sheets

ENDOSCOPE

BACKGROUND OF THE INVENTION

A. Field of the Invention

The present invention relates to an endoscope having an insertion section adapted to be inserted into the body cavity, and more particularly to an endoscope in which a bending portion of the insertion section is bent over a relatively wide range of angle.

B. Description of the Prior Art

To facilitate intra-celial observation, up-to-date endoscopes are designed so that a bending portion of their insertion section can be bent over a wide angular range, or that the minimum available radius of curvature of the bending portion is as small as possible. If the endoscope used is of a direct-view type, therefore, the center of its field of view may possibly be obstructed by a flexible tube of the insertion section when the bending portion is bent at an angle of 180° or more. For a side-view endoscope, the critical bending angle is 90°.

In the recently developed endoscopes, moreover, the bending portion can be bent with a minimum radius of curvature, so that the distance between the distal end portion and the flexible tube of the insertion section is shortened when the bending portion is bent. Accordingly, that area of the view field of the endoscope obstructed by the flexible tube is enlarged further.

Thus, if the bending portion is bent sharply, in a typical conventional endoscope, the center of the view field becomes a dead space, obstructed by the flexible tube of the insertion section. As a result, the observation efficiency of the endoscope is lowered considerably. If the view field is barred by the flexible tube, moreover, only small field portions can be secured for intra-celial observation, on either side of the tube. With use of such a narrow view field, it is difficult to seize the entire image of the object of observation, so that the cause or symptoms of a disease may possibly be overlooked.

Although endoscopes with a bending portion of a narrow maximum bending angle are free from these problems, they are more difficult to operate and lower in observation efficiency than the aforementioned typical one.

SUMMARY OF THE INVENTION

The object of the present invention is to provide an endoscope in which the center of its field of view cannot be obstructed by a flexible tube of its insertion section even when a bending portion of the insertion section is bent sharply.

The above object of the present invention is achieved by an endoscope constructed as follows. The endoscope comprises an observation optical system and an insertion section which includes a bending tube. A plurality of segments, each having a pair of arms at each end portion thereof and rockably connected to one another, are arranged in the bending tube, and wire guides are fixed to the inner peripheral surface of each segment. One end of each of bending control wires is fixed to the segment at the distal end portion of the bending tube. The other end of each wire extends to the proximal end portion of the insertion section, through the wire guides of the other segments. In this arrangement, the bending tube is bent by pulling the other ends of the bending-control wires. The endoscope further includes bending means arranged in the bending tube and adapted to bend, when the bending-control wire is pulled, the bending tube for moving the observation optical system such that the center of the system moves from the center of the insertion section to the periphery thereof.

Thus, in the endoscope of the invention with the construction described above, even though the bending tube is bent sharply, the position of a flexible tube of the insertion section, which may possibly obstruct the field of view, can be shifted to the right or left from the center of the field, thereby keeping the view field entire.

Meanwhile, the field of view of recently developed endoscopes is wide-angled. In the endoscope according to the present invention, therefore, the flexible tube of the insertion section becomes apparently narrow when it is moved to the periphery of the view field. Thus, the endoscope can enjoy a wider field of view.

DETAILED DESCRIPTION OF THE PREFERRED EMBODIMENTS

Preferred embodiments of the present invention will now be described with reference to the accompanying drawings.

Figure 1:
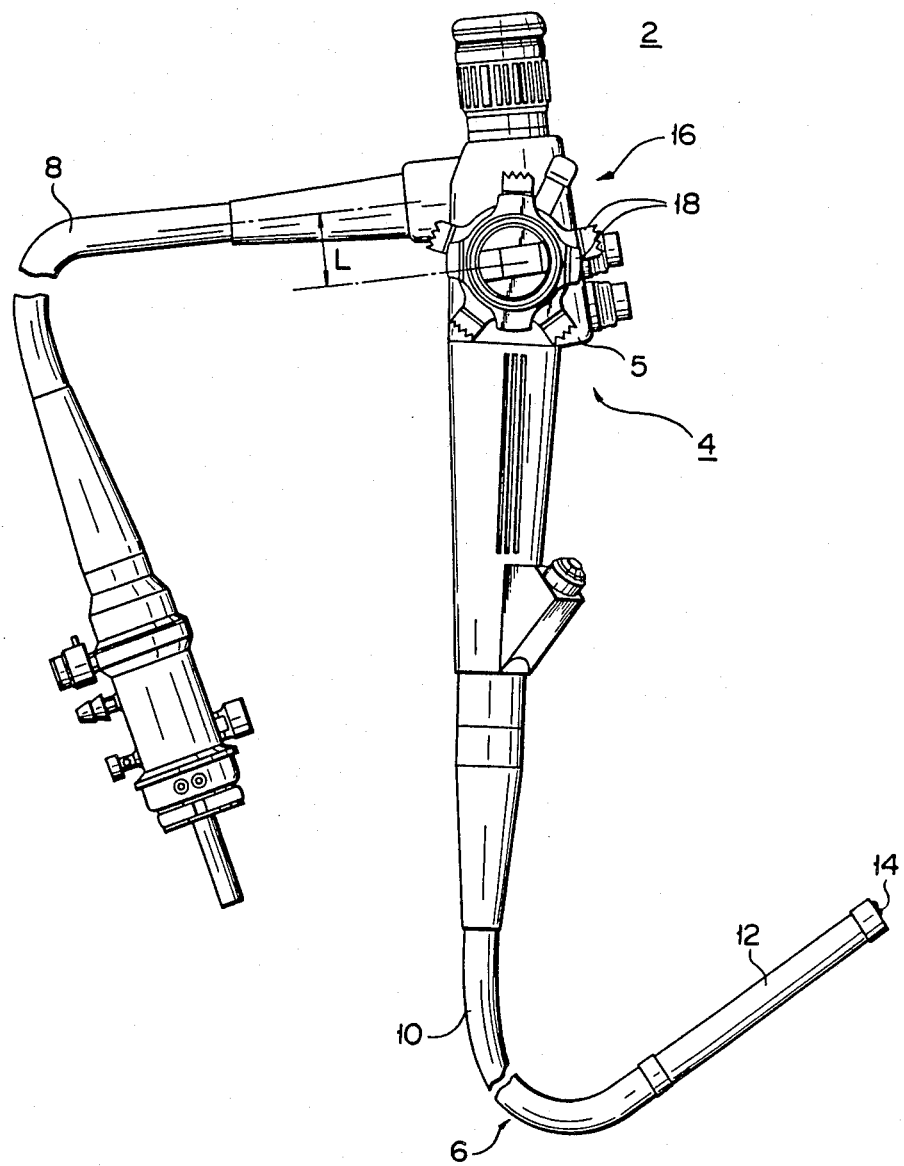
FIG. 1 is a general side view of an endoscope according to the present invention.

FIG. 1 is a general side view of an endoscope according to the present invention. Endoscope 2 comprises control section 4, insertion section 6, and light-guide cable 8. Insertion section 6 includes flexible tube 10, bending tube 12 connected to the distal end of tube 10, and distal end member 14 connected to the distal end of tube 12. Control section 4 is provided with bending-control unit 16 for controlling bending tube 12. Control levers 18 of unit 16 are located outside casing 5 of control section 4. An operator operates levers 18 of control unit 16, thereby controlling bending tube 12 remotely, in order to redirect distal end member 14 both vertically and horizontally. As shown in FIG. 1, moreover, the central axis of each control lever 18 is situated at distance L of about 20 mm from the longitudinal axis of the proximal end portion of light-guide cable 8, with respect to a plane parallel to the drawing plane.

Referring now to FIGS. 2 to 7, a first embodiment of the present invention will be described.

Figure 2:
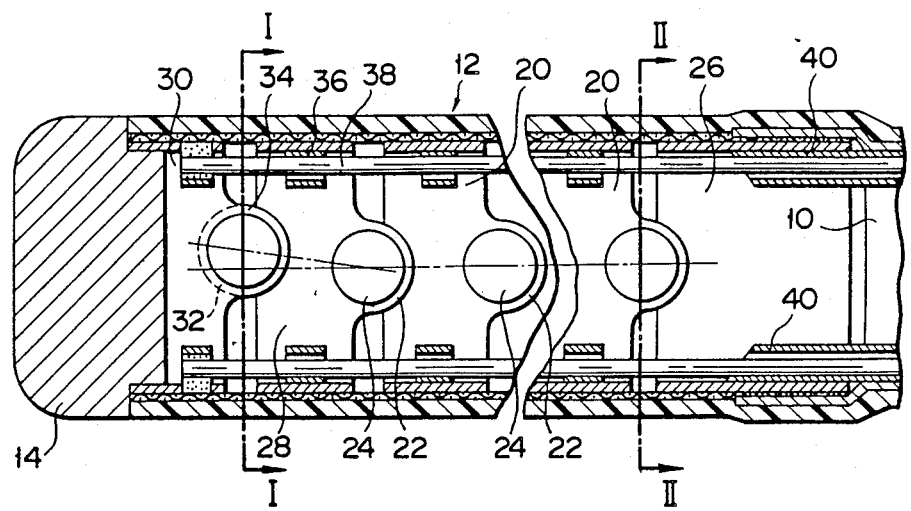
FIG. 2 is a longitudinal sectional view schematically showing an insertion section of an endoscope according to a first embodiment of the invention.
Figure 3:
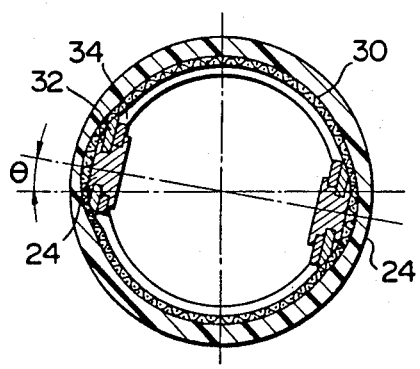
FIG. 3 is a cross-sectional view of the insertion section taken along line I—I of FIG. 2.
Figure 4:
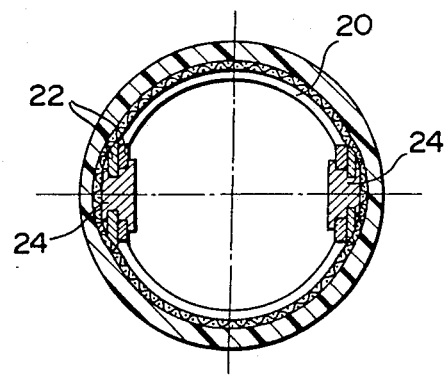
FIG. 4 is a cross-sectional view of the insertion section taken along line II—II of FIG. 2.

As shown in FIG. 2, bending tube 12 includes a plurality of segments. Each of segments 20 of a basic shape has two arms 22 at each end thereof. Each arm 22 is rockably connected to its adjoining segment 20 by means of rivet 24, as shown in FIG. 4. Basic segments 20 are rockably connected in succession, to one another. One end of the chain of segments is fixed to flexible tube 10 by means of mouthpiece 26. The other end of the chain is coupled to distal end member 14 by means of first and second fancy segments 28 and 30. Like segments 20, first fancy segment 28 has two arms at each end thereof. Segment 28 is different from basic segments 20 in arm positions. Arms 22 at one end of first fancy segment 28 are in alignment with their corresponding arms of segments 20. As shown in FIGS. 2 and 3, however, arms 32 at the other end of segment 28 are situated in positions deviated by angle $\theta$, in either the clockwise or counterclockwise direction, from the positions of their corresponding arms 22. Arms 34 are formed at one end of second fancy segment 30. They are connected to their corresponding arms 32 of fancy segment 28 by means of rivets 24, individually. The other end of segment 30 is fixed to distal end member 14.

A plurality of cylindrical wire guides 36 are fixed inside each of segments 20 and first fancy segment 28. Bending-control wires 38 are passed through the wire guides. One end of each wire 38 is fixed to second fancy segment 30, while the other end thereof is connected to its corresponding control lever 18.

Figure 5:
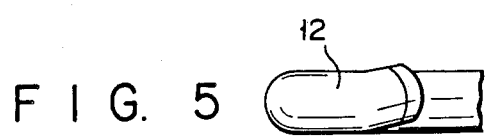
FIG. 5 is a plan view showing a bent state of a bending tube of the insertion section according to the first embodiment.
Figure 6:
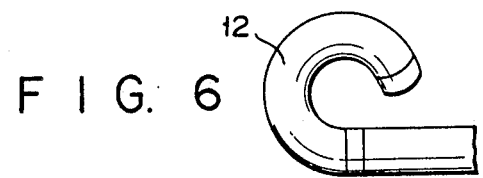
FIG. 6 is a side view of the insertion section shown in FIG. 5.

With this arrangement, if control lever 18 is turned, bending-control wires 38 are pulled toward the proximal end side, and segments 20 are rotated around their corresponding rivets 24. As a result, bending tube 12 bends gradually from its proximal end portion. In doing this, tube 12 starts to bend in a manner such that the proximal-end segment, adjacent to flexible tube 10, rotates first. Thus, the junction between first and second fancy segments 28 and 30 is rotated when bending tube 12 is bent to the maximum, as shown in FIG. 6. Since the axis of rotation of the junction is twisted for a predetermined angle, with respect to those of segments 20, the distal end of bending tube 12 is bent in a direction different from the bending direction of the remaining part, as shown in FIG. 5.

Figure 7:
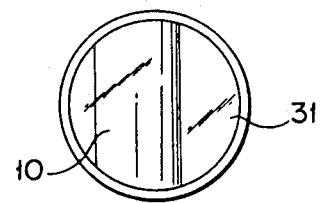
FIG. 7 is a schematic view of the field of view of the endoscope according to the first embodiment.

The field of view of the endoscope, constructed in this manner, will now be described. If the endoscope is of a direct-view type, flexible tube 10 starts to be found in field 31 of the endoscope, as shown in FIG. 7, when the bending angle exceeds 180°. If the endoscope is of a side-view type, the critical bending angle is 90°. As bending tube 12 is bent further, the area ratio of flexible tube 10 to field 31 increases gradually. When second fancy segment 30 is rotated relatively to first fancy segment 28, however, the position of flexible tube 10 in the view field of the endoscope is shifted to the right or left from the center of the field, as shown in FIG. 7.

In the endoscope according to the first embodiment described above, when the bending angle of bending tube 2 is relatively small, tube 12 bends within a plane which passes through its longitudinal axis. When the bending angle approaches its maximum, the bending direction of the distal end portion of tube 12 is shifted to the right or left, thereby securing the view field of the endoscope.

Figure 8:
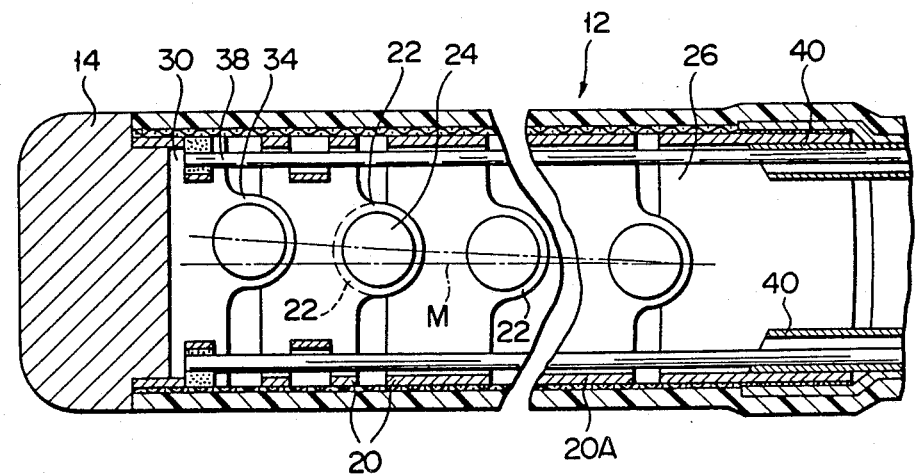
FIG. 8 is a cross-sectional view schematically showing a modification of the insertion section of the endoscope according to of the first embodiment.
Figure 9:
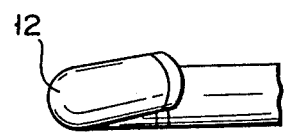
FIG. 9 is a plan view showing a bent state of a bending tube of the insertion section of FIG. 8.

Referring now to FIGS. 8 and 9, a modification of the endoscope according to the first embodiment will be described.

In this modification, arms 22 of a plurality of segments 20 are different in position from one another. More specifically, arms 22 are situated in offset positions, at opposite end portions of the individual segments, with respect to the longitudinal direction thereof. Having their respective pairs of arms 22, segments 20 are connected in a line. Thus, the twist of the arms of the segments, with respect to straight line M, which passes through the center of the junction of segment 20A at the proximal end portion, and extends parallel to the longitudinal axis of flexible tube 10, becomes greater with distance from tube 10.

According to the first embodiment, the bending direction of the distal end portion of bending tube 12 is shifted to the right or left only when tube 12 is bent to the maximum. According to this modification, on the other hand, bending tube 12 is bent in a manner such that its proximal end portion is twisted first, and its distal end portion last, as shown in FIG. 9. Also, when tube 12 is bent, the position of flexible tube 10, as viewed within the view field of the endoscope, is shifted from the center of the field. According to this modification, moreover, bending tube 12 is not yet twisted much by the time flexible tube 10 starts to be found in the view field. At this point of time, the area ratio of tube 10 to the field is so small that the field can be secured fully. As the bending angle increases, the area ratio of the flexible tube also increases gradually. Thereupon, however, the bending direction of bending tube 12 is shifted to the left or right, in an increasing manner. Thus, the view field can always be secured satisfactorily.

In the modification described above, furthermore, bending tube 12 gradually changes its bending direction as it bends. Accordingly, the cause or symptoms of a disease cannot be overlooked even if the view field is moved suddenly.

Figure 10:
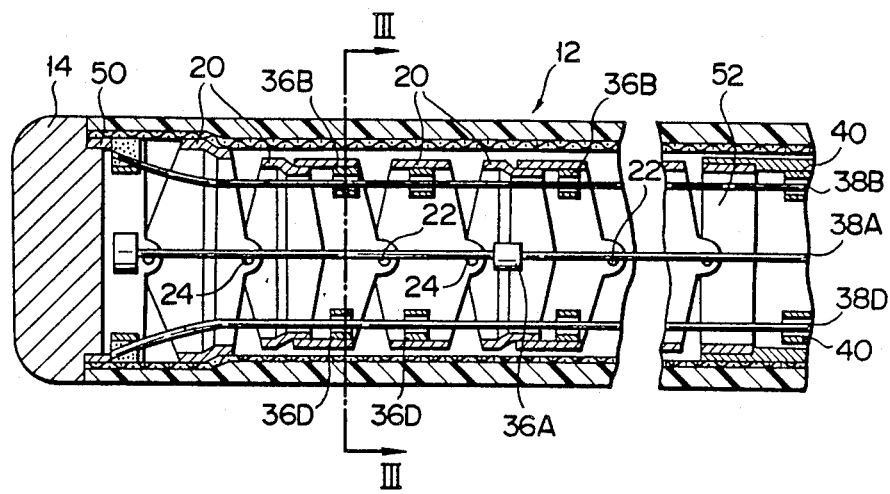
FIG. 10 is a longitudinal sectional view schematically showing an insertion section of an endoscope according to a second embodiment of the invention.
Figure 11:
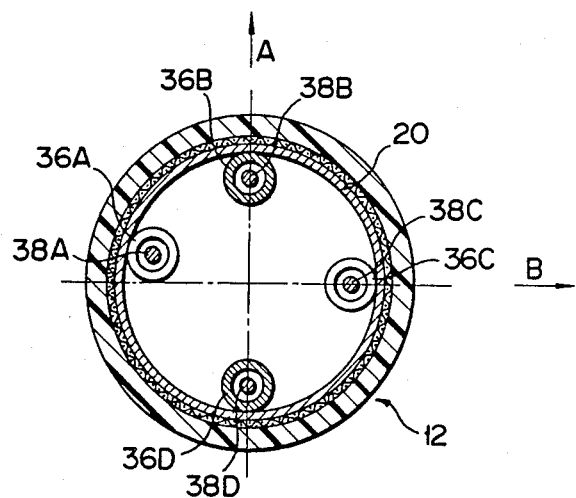
FIG. 11 is a cross-sectional view of the insertion section taken along line III—III of FIG. 10.

FIGS. 10 and 11 show an endoscope according to a second embodiment of the present invention. In this embodiment, bending tube 12 includes a plurality of segments 20. Arms 22, which protrude individually from two opposite end portions of the peripheral wall of each segment 20, are rockably connected to their corresponding arms of each adjacent segment 20, by means of rivets 24. Leading segment 50 is fixed to distal end member 14, while trailing segment 52 is fixedly connected to flexible tube 10. Four cylindrical wire guides 36A, 36B, 36C and 36D are fixed to the inner peripheral surface of each segment 20. Four bending-control wires 38A, 38B, 38C and 38D are passed through guides 36A, 36B, 36C and 36D, respectively. One end of each control wire is fixed to leading segment 50, while the other end thereof is connected to bending-control unit 16. Thus, by pulling any of the bending-control wires toward its proximal end portion, bending tube 12 can be bent toward the pulled wire.

In the endoscope according to the second embodiment, as shown in FIG. 11, wire guides 36A, 36B, 36C and 36D are arranged on the inner peripheral surface of each segment 20, at intervals of about 90°. However, one of guides 36A and 36C, arranged on a plane perpendicular to the direction of arrow A in which tube 12 is to be bent to the maximum, is biased in direction A. With this arrangement, if bending-control wire 38B on the side of the maximum-bending direction is pulled toward its proximal-end side so that bending tube 2 is bent in direction A, a wire passage, which is defined by biased wire guides 36A, shortens. As a result, wire 38A, passed through the passage, is urged to move for the reduced length toward flexible tube 10, through wire guides 36A and guide pipe 40. However, the frictional resistance between wire 38A and pipe 40 in tube 10 is too high for wire 38A to move in tube 10. Accordingly, bending tube 12 is bent in the direction of arrow B or in the direction opposite to the location of wire 38A, so that the wire passage is restored to its original length. When tube 12 is bent to the maximum, therefore, the bending direction of its distal end portion is changed to a vertical direction. Thus, just as in the case of the first embodiment, the position of flexible tube 10, as viewed in the view field of the endoscope, is moved from the center of the field to the periphery thereof.

Figure 12:
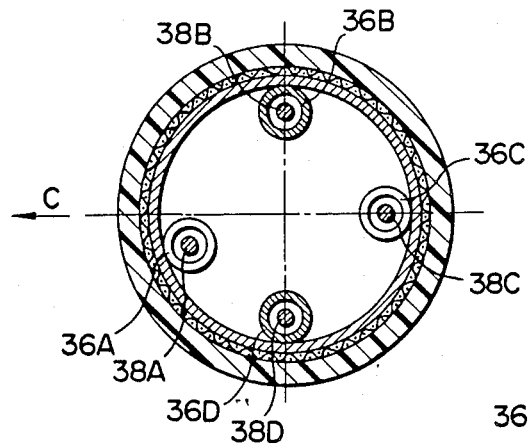
FIG. 12 is a cross-sectional view showing a first modification of the insertion section of the endoscope according to the second embodiment.

FIG. 12 shows a first modification of the endoscope according to the second embodiment. In this modification, one of guides 36A and 36C, which are arranged on a plane perpendicular to the maximum bending direction indicated by arrow A in FIG. 11, is biased in the direction opposite to the maximum-bending direction.

Thus, in this endoscope, if bending-control wire 38B on the side of the maximum-bending direction is pulled, the wire passage, defined by biased wire guides 36A, lengthens. As a result, bending-control wire 38A is urged to be drawn out of flexible tube 10 for the extended length. However, the frictional resistance between wire 38A in tube 10 and guide pipe 40 is too high for wire 38A to move in tube 10. Accordingly, bending tube 12 is bent in the direction of arrow C or on the side of wire 38A, so that the wire passage is restored to its original length. Thus, the same effect of the second embodiment can be obtained.

Figure 13:
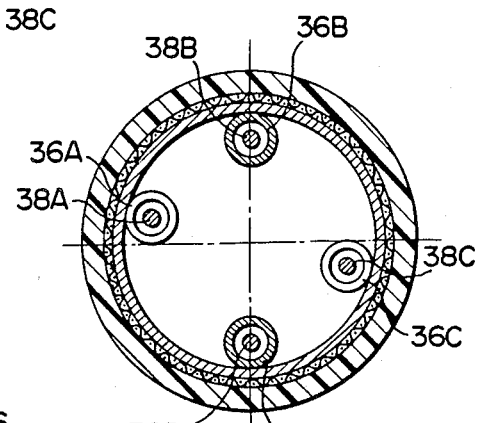
FIG. 13 is a cross-sectional view showing a second modification of the insertion section of the endoscope according to the second embodiment.

FIG. 13 shows a second modification of the second embodiment.

In this modification, wire guide 36A on a plane perpendicular to the maximum-bending direction is biased in the maximum-bending direction, while guide 36C is biased in the opposite direction.

Thus, according to the second modification, the position of flexible tube 10, as viewed in the view field of the endoscope, is moved greatly from the center of the field to the periphery thereof.

Figure 14:
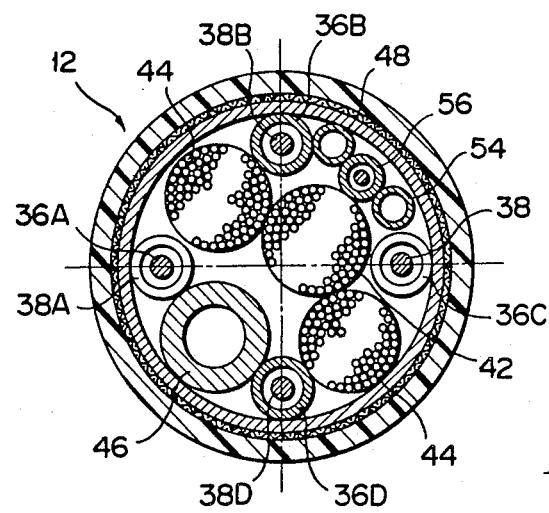
FIG. 14 is a cross-sectional view schematically showing an insertion section of an endoscope according to a third embodiment of the invention.
Figure 15:
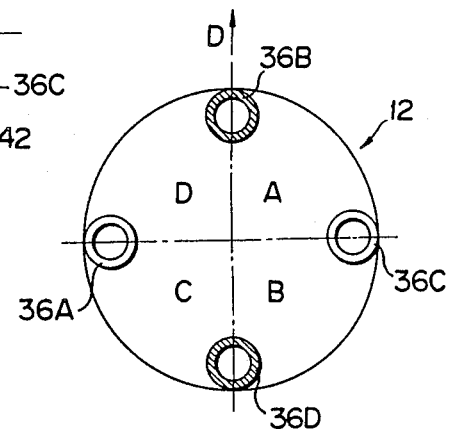
FIG. 15 is a schematic view for illustrating the configuration of the endoscope according to the third embodiment.

Referring now to FIGS. 14 and 15, an endoscope according to a third embodiment of the present invention will be described. Generally, bending tube 12 of insertion section 6 of the endoscope contains therein first and second transmission members 42 and 44, instrument channel 46, water-feed tube 48, air-feed tube 54, and control wire 56. Member 42 is used to transmit an image from the distal end portion of insertion section 6, while member 44 is used to transmit an illumination light to the distal end portion. A medical instrument is to be inserted into channel 46. Tubes 48 and 54 are used to feed the distal end portion with water and air, respectively. Wire 56 serves as means for controlling a forceps raising device. As shown in FIG. 15, the cross section of bending tube 12 is divided into four regions A, B, C and D by two straight lines which individually connect wire guides 36B and 36D, arranged in vertical relation, and wire guides 36A and 36C in horizontal relation. In this embodiment, instrument channel 46, water- and airfeed tubes 48 and 54, and control wire 56, all of which are relatively high in rigidity, are located in two nonadjacent regions, e.g., regions A and C.

Thus, if any one of four bending-control wires 38A, 38B, 38C and 38D is pulled, bending tube 12 is bent toward the side the pulled wire. In this case, the path length for each built-in member contained in tube 12, that is, the distance from the distal end of the member to the rear end of tube 12, varies depending on the location of the member. If the space inside bending tube 12 is divided into two equal parts, i.e., regions nearer to and farther from the center of curvature of tube 12 in a bent state, the path length is reduced for the members within the nearer region, and is extended for the members within the farther region. To cope with the variation of the path length, the built-in members may move in the longitudinal direction or toward the center of curvature, or may extend or contract. However, recently developed endoscopes are confronted with two contradictory requirements; a reduction of the outside diameter of the insertion section for the relief of a patient's pain, and an increase in thickness of the built-in members for a higher performance. To fulfill these requirements, the built-in members are squeezed into the whole area of the bending tube except irreducible necessary spaces. Thus, the movement of one member is restricted by the other members, and each member can move only within a very narrow range, in the longitudinal direction or toward the center of curvature. Mostly, therefore, the built-in members are designed so as to extend or contract themselves. Although those members with relatively low rigidity can extend or contract with ease, those ones with relatively high-rigidity cannot. Thus, the high-rigidity members cannot absorb the variation of the path length during the bending operation, and cause bending tube 12 to bend in a direction perpendicular to a plane which passes through the longitudinal axis of tube 12.

The operation of the endoscope, constructed in this manner, will now be described. As shown in FIG. 15, the inside of bending tube 12 is divided into four regions A, B, C and D by the two straight lines which connect wire guides 36A and 36C and guides 36B and 36D, situated at opposite ends. Regions A, B, C and D are arranged circumferentially in the clockwise direction. If bending tube 12 is bent in any direction, as indicated by arrow D, wire guide 36B, which is nearest to the center of curvature, is situated between regions A and D. If the high-rigidity built-in members are disposed in region A or D, they are subjected to a compressive force when tube 12 is bent. By this compressive force, tube 12 is bent on the side opposite to the high-rigidity members. If the high-rigidity members are disposed in region B or C, on the other hand, they are subjected to a tractive force when bending tube 12 is bent in the direction of arrow D. By this tractive force, tube 12 is bent on the side of the high-rigidity members.

If the high-rigidity members are located intensively in the domain combining regions A and C or in the domain combining regions B and C, they all act so as to urge bending tube 12 to bend in one direction perpendicular to its bending direction when tube 12 is bent in any direction. As a result, bending tube 12 bends in the perpendicular direction, thereby absorbing the change of the path length for the members. At the same time, the position of flexible tube 10, as viewed in the view field of the endoscope, is moved from the center of the field to the periphery thereof, by the bending action of tube 12. Thus, the view field for observation can be maintained.

When the bending tube is bent in a predetermined direction, in the endoscope according to the third embodiment, the compressive or tractive force acting on the high-rigidity built-in members causes the bending tube to bend in a direction perpendicular to the predetermined bending direction. In this manner, such an extra force can be eliminated. Thus, the bending tube can be operated without applying any unreasonable force to the members contained therein, so that damage to the built-in members can be reduced.

What is claimed is:

1. An endoscope with an observation optical system and an insertion section including a bending tube, comprising:
    a plurality of segments arranged in the bending tube, each having a pair of arms at each end portion thereof, said segments being connected at the arms, and rotatable with respect to one another;
    wire guides fixed to the inner peripheral surface of each segment;
    a bending-control wire having one end fixed to the segment at the distal end portion of the bending tube, and the other end extending through the wire guides of the other segments to the proximal end portion of the insertion section, said bending tube being bent when the other end of the wire is pulled; and
    bending means in the bending tube for bending when the bending-control wire is pulled, the bending means comprising the segments; a first fancy segment having first arms, at one end thereof, rockably connected to the distal end of the segments, and second arms, at the other end thereof, situated in positions deviated by a predetermined angle from the positions of the first arms; and a second fancy segment fixed to the distal end portion of the bending tube, and having arms rockably connected to the second arms of the first fancy segment.

2. An endoscope with an observation optical system and an insertion section including a bending tube, comprising:
    a plurality of segments arranged in the bending tube, each having a pair of arms at each end portion thereof, said segments being connected at the arms, and rotatable with respect to one another;
    wire guides fixed to the inner peripheral surface of each segment;
    a bending-control wire having one end fixed to the segment at the distal end portion of the bending tube, and the other end extending through the wire guides of the other segments to the proximal end portion of the insertion section, said bending tube being bent when the other end of the wire is pulled; and bending means in the bending tube for bending when the bending-control wire is pulled, the bending means comprising the segment connected to the proximal end portion of the bending tube; a plurality of first fancy segments connected in a line, and each having first arms rockably connected to the arms of each adjacent segment, said second arms situated in positions deviated by a predetermined angle from the positions of the first arms; and a second fancy segment fixed to the distal end portion of the bending tube, and having arms rockably connected to the second arms of the first fancy segment.

3. An endoscope with an observation optical system and an insertion section including a bending tube, comprising:
    a plurality of segments arranged in the bending tube, each having a pair of arms at each end portion thereof, said segments being connected at the arms, and rotatable with respect to one another;
    wire guides fixed to the inner peripheral surface of each segment;
    a bending-control wire having one end fixed to the segment at the distal end portion of the bending tube, and the other end extending through the wire guides of the other segments to the proximal end portion of the insertion section, said bending tube being bent when the other end of the wire is pulled; and bending means in the bending tube for bending when the bending-control wire is pulled, the bending means comprising one wire guide disposed on a plane perpendicular to the bending direction, an outer surface of the insertion section being within a view field of the observation optical system when the bending tube is bent at a maximum angle in the bending direction, and the other wire guide biased in the bending direction from the perpendicular plane.

4. An endoscope with an observation optical system and an insertion section including a bending tube, comprising:
    a plurality of segments arranged in the bending tube, each having a pair of arms at each end portion thereof, said segments being connected at the arms, and rotatable with respect to one another;
    wire guides fixed to the inner peripheral surface of each segment;
    a bending-control wire having one end fixed to the segment at the distal end portion of the bending tube, and the other end extending through the wire guides of the other segments to the proximal end portion of the insertion section, said bending tube being bent when the other end of the wire is pulled; and bending means in the bending tube for bending when the bending-control wire is pulled, the bending means comprising one wire guide disposed on a plane perpendicular to the bending direction, an outer surface of the insertion section being within a view field of the observation optical system when the bending tube is bent at a maximum angle in the bending direction, and the other wire guide biased in the direction opposite to the bending direction from the perpendicular plane.

5. An endoscope with an observation optical system and an insertion section including a bending tube, comprising:
    a plurality of segments arranged in the bending tube, each having a pair of arms at each end portion thereof, said segments being connected at the arms, and rotatable with respect to one another;
    wire guides fixed to the inner peripheral surface of each segment;
    a bending-control wire having one end fixed to the segment at the distal end portion of the bending tube, and the other end extending through the wire guides of the other segments to the proximal end portion of the insertion section, said bending tube being bent when the other end of the wire is pulled; and bending means in the bending tube for bending when the bending-control wire is pulled, the bending means comprising one wire guide biased in the bending direction of the bending tube from a plane perpendicular to the bending direction, an outer surface of the insertion section being within a view field of the observation optical system when the bending tube is bent at a maximum angle in the bending direction, and the other wire guide biased in the direction opposite to the bending direction from the perpendicular plane.

* * * * *